United States Patent
Hart et al.

(10) Patent No.: US 6,183,503 B1
(45) Date of Patent: Feb. 6, 2001

(54) MESH STENT WITH VARIABLE HOOP STRENGTH

(75) Inventors: Charles C. Hart, Huntington Beach; John Brustad, Dana Point; Said Hilal, Coto de Caza, all of CA (US)

(73) Assignee: Applied Medical Resources Corporation, Rancho Santa Margarita, CA (US)

( * ) Notice: Under 35 U.S.C. 154(b), the term of this patent shall be extended for 0 days.

(21) Appl. No.: 09/399,211

(22) Filed: Sep. 17, 1999

(51) Int. Cl.[7] ........................................................ A61F 2/06
(52) U.S. Cl. .............................................. 623/1.1; 606/198
(58) Field of Search ................................... 623/1.51, 1.49, 623/1.5, 1.15, 1.1, 1.11, 11, 12, 13; 606/198, 194, 192; 604/8

(56) References Cited

U.S. PATENT DOCUMENTS 5,007,926 * 4/1991 Derbyshire ................................ 623/1
6,001,117 * 12/1999 Huxel et al. ........................ 606/191

* cited by examiner

Primary Examiner—Michael Buiz
Assistant Examiner—Anthony S. King

(57) ABSTRACT

A stent is adapted for disposition in a body conduit of a patient and comprises a mesh formed in the configuration of a tube and having an axis and axial convolutions, which facilitate movement between a low-profile state and a high-profile state. The tube in the low-profile state has an elongate configuration and a wall with a first thickness and first tube strength. The tube in the high-profile state has a compressed configuration and a wall with a second thickness greater than the first thickness and a second hoop strength greater than the first hoop strength. An associated method of use includes the steps of mounting the step on a catheter between first and second enlargement members, increasing the size of the enlargement members, and moving the enlargement members to axially compress the stent to the high-profile state. An associated method of manufacture includes the steps of corrugating the mesh on a mandrel by moving the ends of the mesh toward each other. The mesh can then be heat-set in the high-profile state.

10 Claims, 3 Drawing Sheets

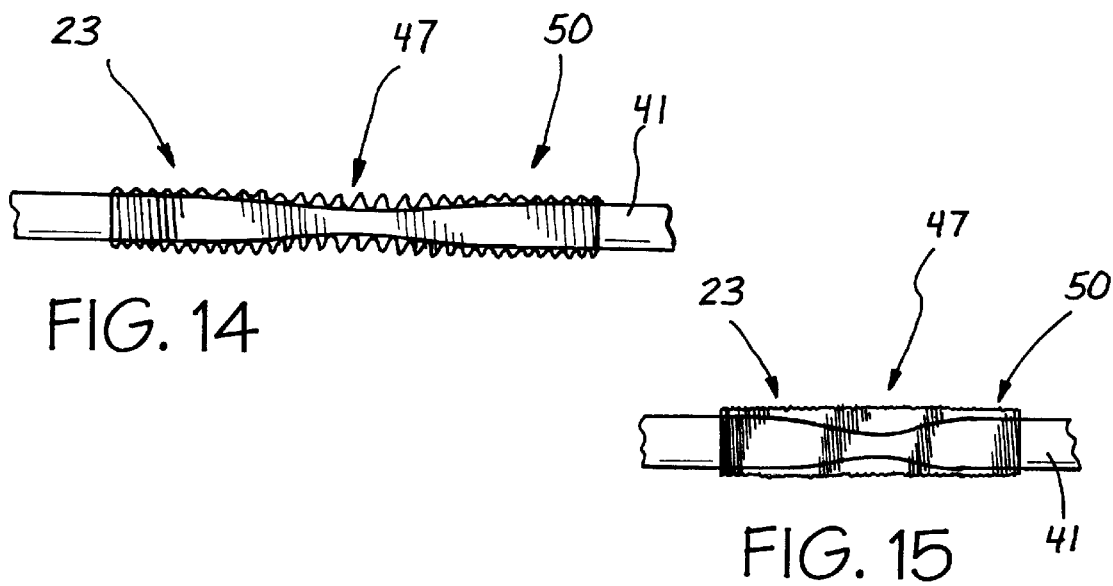
FIG. 14
FIG. 15
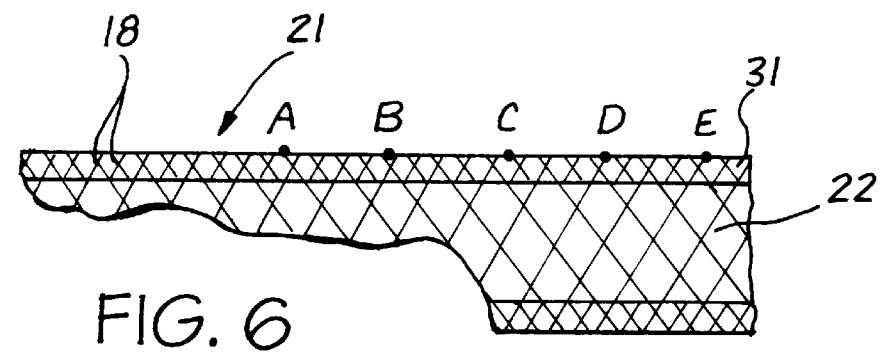
FIG. 6
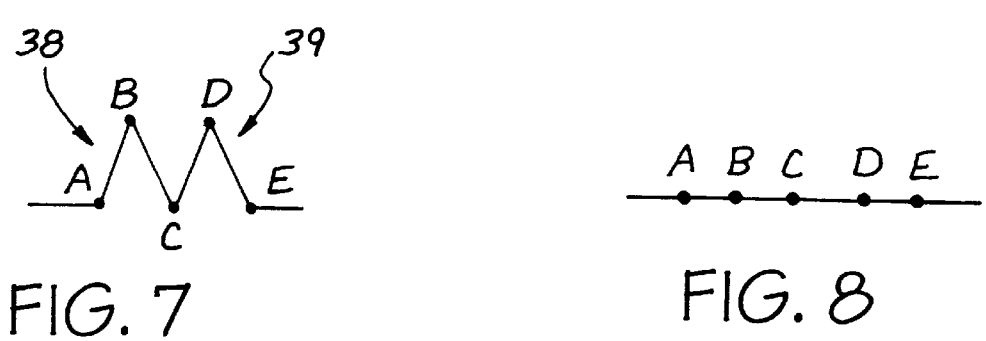
FIG. 7
FIG. 8
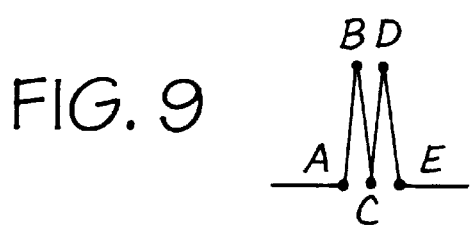
FIG. 9

MESH STENT WITH VARIABLE HOOP STRENGTH

BACKGROUND OF THE INVENTION

1. Field of the Invention

This invention relates generally to stents adapted for use in providing structural support for the walls of body conduits.

2. Discussion of the Prior Art

Stents have been widely used in the body to provide structural support for the walls of body conduits. For example, stents have been used in the field of urology to provide structural support for the urethra, particularly in proximity to the prostate. Vascular stents have been particularly adapted for use in both veins and arteries to add support to weakened vascular walls, for example, in proximity to aneurysms. In each of these cases, the stent provides a tubular structure with sufficient hoop strength to support the walls while maintaining patency of the conduit.

Stents of the past have typically been provided in the form of a tube having a low-profile state facilitating insertion, and characteristics for being expanded to a high-profile state to provide structural support and lumen patency. Stents have been formed from various plastics, as well as a variety of metals and alloys. In some cases, stents have been formed as a tubular mesh that facilitates movement between the low-profile and high-profile states. Such a stent is disclosed and claimed in applicant's U.S. patent application Ser. No. 09/303,113, filed on Apr. 30, 1999, and entitled "Improved Ureteral Stent System Apparatus and Method," which is incorporated herein by reference.

In order for the tubular stents to be formed of solid materials and also be expandable, the walls of the stents have needed to be cut, sometimes in intricate patterns, in order to facilitate expansion. Particularly in the case of metal stents, these small intricate patterns have been cut by lasers in an expensive and time-consuming fabrication process.

In accordance with one surgical operation, such a stent has been mounted over the balloon of a catheter and inserted in the low-profile state into the femoral artery. Then the catheter is advanced until the stent is moved into the desired location. At this point, the balloon as been inflated within the stent, moving its walls outwardly to the high-profile state. Then the balloon is deflated and the catheter withdrawn, leaving the stent to structurally support the body conduit.

The metal stents have been particularly desirable for their high hoop strength. Unfortunately, to provide such stents with the expansion characteristics desired, an intricate fabrication process is required. This, of course, adds to the expense associated with this type of stent.

SUMMARY OF THE INVENTION

The stent of the present invention overcomes these deficiencies of the prior art. It can be formed from inexpensive plastic filaments and woven to form a tubular mesh having a low-profile and a high-profile state. The mesh can be axially corrugated to further facilitate movement between these two states. In the high-profile state, the corrugations of the tube increase the thickness of the tubular wall, greatly enhancing its hoop strength. The stent can be easily manufactured at a greatly reduced cost of fabrication. In operation, the stent of the present invention can be inserted easily over a telescoping catheter having dual balloons. The balloons can be inflated and telescoped together to axially compress and radially expand the stent to the high-profile state. The balloons can then be deflated and the catheter withdrawn. When the stent is manufactured of thermoplastics, it can be heat-set so that it is automatically biased to the high-profile state.

In one aspect of the invention, a vascular stent is adapted to be disposed in the blood vessel of a patient. This stent includes a mesh formed in the configuration of a tube having an axis, the tube being expandable from a low-profile state to a high-profile state. The tube in the low-profile state has an elongate configuration with a wall having a first thickness and a first hoop strength. The tube in a high-profile state has a compressed configuration with the wall having a second thickness greater than the first thickness and a second hoop strength greater than the first hoop strength. The tube is formed with a plurality of convolutions, which are spaced in the low-profile state and non-spaced in the high-profile state.

In another aspect, the invention includes a vascular stent, including a tube formed in the configuration of a weave having a thickness and a plurality of convolutions facilitating movement of the tube between an insertion state and an operative state. The tube in the insertion state being stretched along the axis and having a first wall thickness generally equivalent to the thickness of the weave. The tube in the operative state being compressed axially to a length generally equivalent to twice the thickness of the weave multiplied by the number of convolutions.

In an additional aspect, the stent is adapted to be placed in a body conduit and includes a plurality of filaments forming a mesh with a first thickness, the mesh being disposed in the configuration of a tube having an axis. The tube is axially corrugated to facilitate movement between a low-profile state with a first wall thickness and high-profile state with a second wall thickness greater than the first wall thickness.

A further aspect of the invention relates to a method for using a stent to support a body conduit. The method includes the step of providing a stent having a woven tubular configuration with a plurality of convolutions disposed along an axis of the stent. A catheter is provided with an axis, and a first enlargement member together with a second enlargement member that are axially moveable relative to each other. The stent is mounted on the catheter between the first enlargement member and the second enlargement member. Then the catheter and the stent are inserted into the blood vessel with the stent in a low-profile state and having a first hoop strength. The size of each enlargement member is then increased and the members moved toward each other. This axially compresses the stent and provide the stent with the second hoop strength.

These and other features and advantages of the invention will become more apparent with a discussion of specific embodiments of the invention and reference to the associated drawings.

DESCRIPTION OF THE DRAWINGS

FIG. 6 is a schematic view illustrating five positions along a wall of the stent;

FIG. 7 is a schematic view showing the five positions with the stent in a normal state;

FIG. 8 is a schematic view showing the five positions when the stent is in a low-profile state; and FIG. 9 is a schematic view showing the five positions when the stent is in the high-profile state.

FIG. 10–FIG. 15 are side-elevation views of a method for manufacturing the stent of the present invention;

FIG. 10 is a side-elevation view of a tubular mesh being moved over a mandrel;

FIG. 11 is a side-elevation view of the tubular mesh being axially compressed on the mandrel to form the corrugations of the stent;

FIG. 12 is a side-elevation view of the corrugated stent on the mandrel, being heat-set to the high-profile state;

FIG. 13 is a side-elevation view of the corrugated stent in the high-profile state;

FIG. 14 is a side-elevation view of a stent with a variable diameter for producing a stent having corrugations of different size; and FIG. 15 is a side-elevation view similar to FIG. 14 showing the stent axially compressed with corrugations of different size.

DESCRIPTION OF PREFERRED EMBODIMENTS AND BEST MODE OF THE INVENTION

Figure 1:
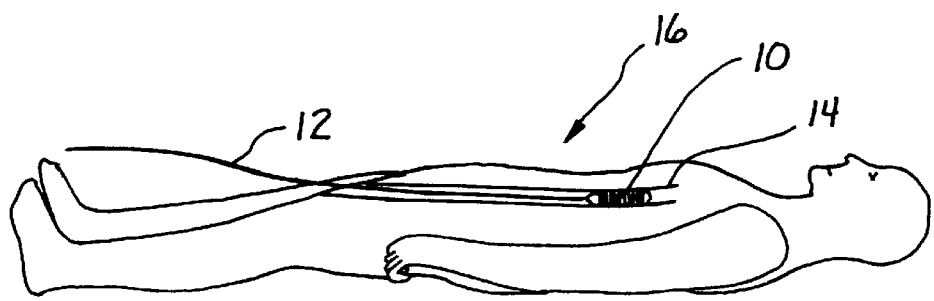
FIG. 1 is a perspective view of a patient and a catheter of the present invention positioned to deploy a corrugated stent of the present invention.

A vascular stent is illustrated in FIG. 1 and designated generally by the reference numeral 10. In this view, the stent 10 is mounted on a catheter 12 and inserted into a femoral artery 14 of a patient 16 in order to repair or strengthen the wall of the artery 14. Although FIG. 1 illustrates use of the stent 10 in a vascular environment, it will be apparent that the vascular stent 10 is merely representative of any stent, which might be used to repair or strengthen the wall of a body conduit. By way of example, body conduits other than the femoral artery 14 might include a urinary conduit, such as a urethra, or an airway, such as the trachea.

In general, all such stents, including the vascular stent 10, will include a plurality of filaments 18 that are formed into a mesh 21 having interstices 22 and the shape of a tube 23 having an axis 25. The tube 23 will typically have a first end 27 axially spaced from a second end 28.

The mesh 21 that forms the tube 23 can be provided with a multiplicity of corrugations 29 along the axis 25. Each of these corrugations 29 is disposed generally in a radial plane, such as the plane 30. These corrugations 29 provide the tube 23 with a wall 31 having a thickness that is variable, as described in greater detail, below. The mesh 21 may be non-woven or woven as in the illustrated embodiment.

Figure 2:
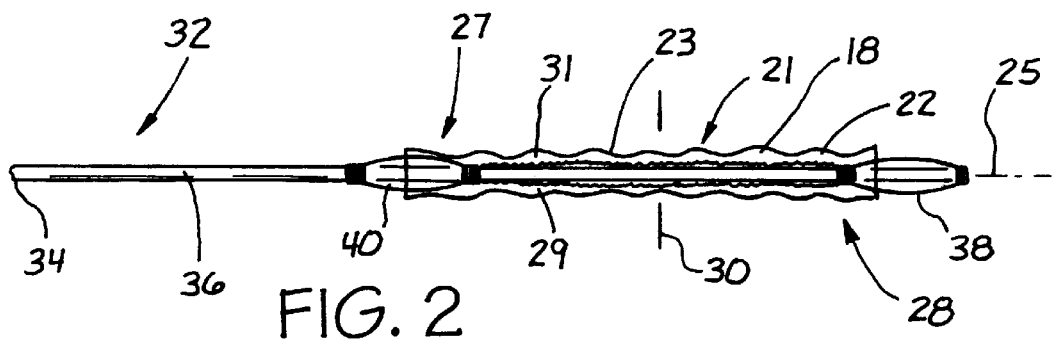
FIG. 2 is a side-elevation view of the stent mounted on the insertion catheter in the low-profile state.

With reference to FIG. 2, it can be seen that the catheter 12 in a preferred embodiment includes a telescoping shaft 32 that is formed with an inner tube 34 moveable within an outer tube 36. A distal balloon 38 is attached to the inner tube 34 and inflatable through the lumen of the inner tube 34. A proximal balloon 41 is attached to the distal end of the outer tube 36 and inflatable between the inner tube 34 and the outer tube 36. In a preferred method, the stent 10 is mounted between the balloons 38 and 41.

Figure 3:
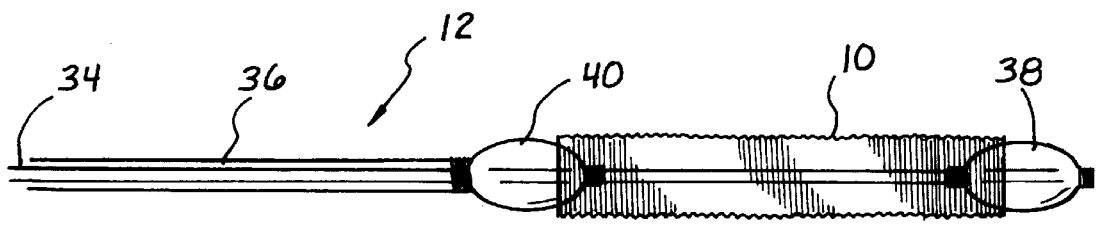
FIG. 3 is a side-elevation view of the catheter balloons expanded and axially converged to move the stent toward the high-profile state.
Figure 4:
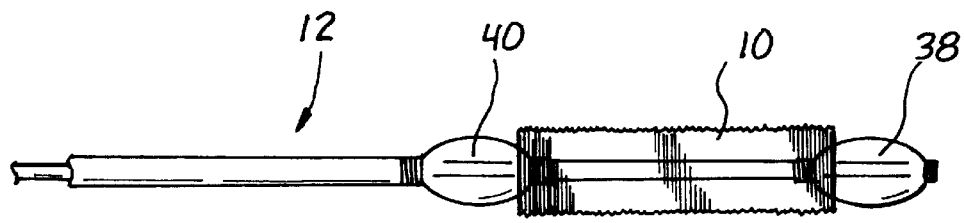
FIG. 4 is a side-elevation view of the stent in the high-profile state.

In the illustrated embodiment one of the factors which affects the thickness of the wall 31 is the general profile of the stent 10. For example, the stent 10 can be axially expandable to a low-profile state, as illustrated in FIG. 3, and axially compressible to a high-profile state, as illustrated in FIG. 4. In the low-profile state, the corrugations 29 are spaced and the interstices 22 of the mesh 21 are generally open. In the high-profile state, the corrugations are contacting and the interstices 22 of the mesh 21 are generally closed.

As noted, the vascular stent 10 can be operatively disposed using the catheter 12. With the stent 10 mounted between the balloons 38 and 41 and expanded to the low-profile state, the catheter 12 and stent 10 are easily insertable into the femoral artery 14. Once the stent is in place, the balloons 38 and 41 can be inflated and the inner cannula 34 can be moved proximally relative to the outer cannula 36. This moves the balloons 38 and 41 into proximity with the ends 27 and 28, axially compressing the stent 10 as illustrated in FIG. 4.

Figure 5:
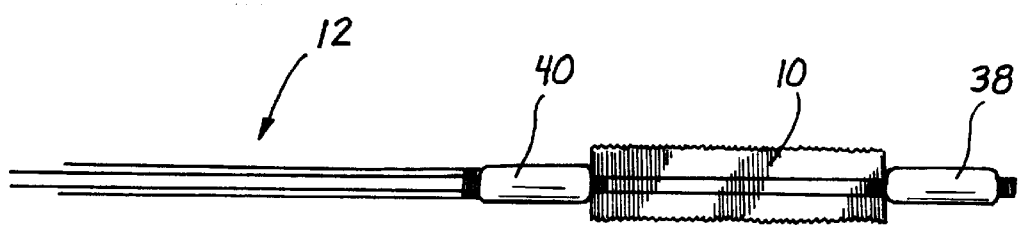
FIG. 5 is a side-elevation view with the catheter balloons deflated facilitating removal of the catheter from the stent.

After the stent 10 has been formed into its high-profile state, the balloons 38 and 41 of the catheter 12 can be deflated, as illustrated in FIG. 5, and the catheter 12 can be removed proximally leaving the stent 10 operatively disposed within the artery 14 in its high-profile state.

The corrugations 29 are of particular interest to the present invention. The advantages provided by the corrugations 29 will be most appreciated with reference to the schematic views of FIGS. 6–9. For example, in FIG. 6, one wall 31 of the tubular stent 10 is illustrated with points A, B, C, D, and E axially spaced along the wall 31. The filaments 18 forming the mesh 21 and defining the interstices 22 are also shown in this view.

When the wall 31 is corrugated, the points A–E along the wall 31 form individual corrugations designated by the reference numerals 38 and 39 in FIG. 7. From this view it can be seen that the points B and D of the corrugations 38 and 39 define the outer diameter of the wall 31 forming the tube 23. Similarly, the points A, C, and E define the inner diameter of the wall 31. It is the distance between these alternating points, B and D, on the outside, and A, C, and E, on the inside, that defines the thickness of the wall 31.

When the tube 23 is axially stretched or elongated, the filaments 18 forming the mesh 21 tend to move into a generally parallel orientation drawing the tube 23 into the low-profile state. The corrugations 29 also facilitate this elongation, as illustrated in FIG. 8. In this view it can be seen that the individual corrugations 38 and 39 practically disappear as the points A–E align. In the resulting low-profile state, the thickness of the wall 31 is generally equal to twice the diameter of the filaments 18. In other words, the wall 31 has a thickness generally equivalent to that of the mesh 21.

When the tube 23 is axially compressed, the corrugations 29 are not only formed, but also radially compacted so that the interstices 22 are filled by adjacent filaments 18. As illustrated in FIG. 9, the alternating points B and D (on the outside) and points A, C, and E (on the inside) are brought into close proximity. In this configuration, the wall 31 has a high-filament density and a maximum thickness generally equal to the distance separating the adjacent points, such as the points A and B, or points B and C.

With the corrugations 29 closely compacted, the tube 23 has a high-profile and a maximum thickness for the wall 31. It has been found that this increased thickness of the wall 31 greatly increases the hoop strength of the stent 10 in the high-profile state. Appreciating that it is the strength of the stent 10 that is relied on to add structural rigidity to the artery 14, this increased hoop strength is of particular advantage.

The stent 10 can now be made from plastic materials that are much less expensive and much more easily fabricated than the metal materials of the past.

Figure 10:
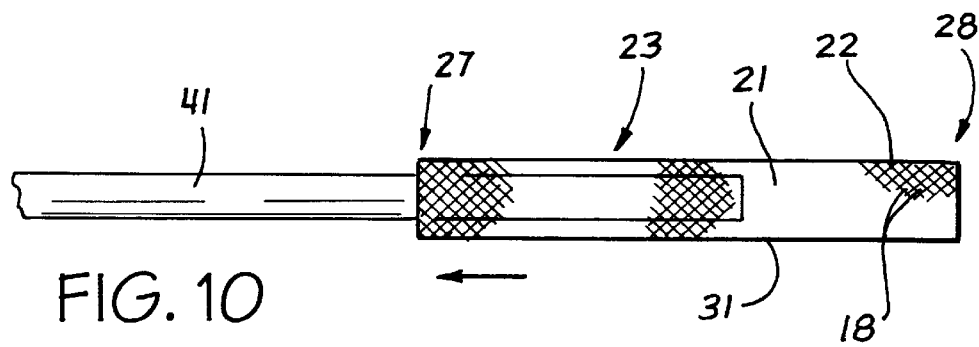
Figure 11:
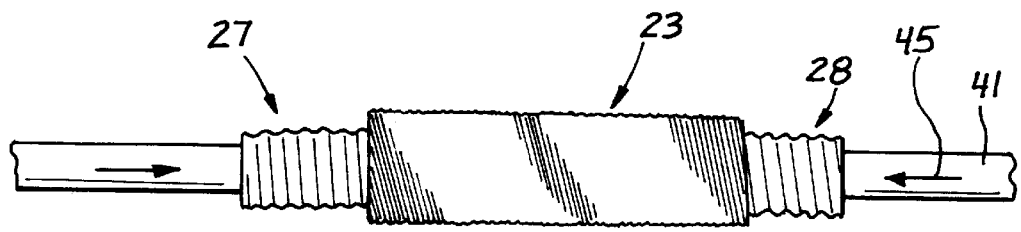

Steps in preferred methods of manufacturing the stent 10 are illustrated in FIGS. 10–15. In FIG. 10, for example, a mandrel is provided along with a cylindrical piece of the mesh 21. As noted, this mesh 21 is provided in the form of a tube 23 having the first end 27 and the second end 28. At this point, the thickness of the wall 31 of the tube 23 is dependent upon the diameter of the filaments 18 that form the mesh 21. Where these filaments 18 cross, the wall 31 has a thickness equal to twice the diameter of the filaments 18. The tubular mesh 21 is inserted over the mandrel 41 in an initial step of this manufacturing process.

After the tube 23 has been positioned on the mandrel 41, the ends 27 and 28 can be moved toward each other, as indicated by arrows 43 and 45. Initially, this axial compression will be accommodated by movement of the filament 18 with no change in the thickness of the wall 31. Surprisingly, however, further axial compression will cause the mesh 21 to form the corrugations 29. These corrugations 29 will tend to extend inwardly until the inside diameter of the tube 23 is generally equivalent to the outside diameter of the mandrel 41. This step of forming the corrugations 29, of course, increases the thickness of the wall 31 with the resulting increase in hoop strength in this high-profile state.

Figure 12:
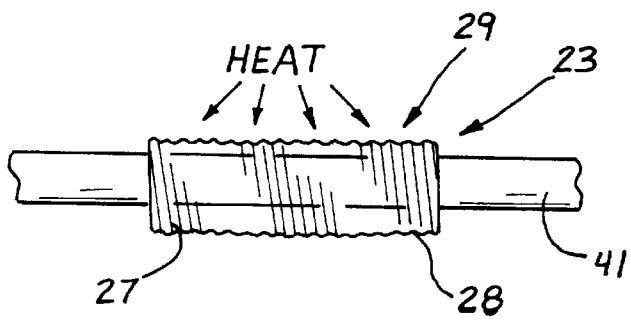
Figure 13:
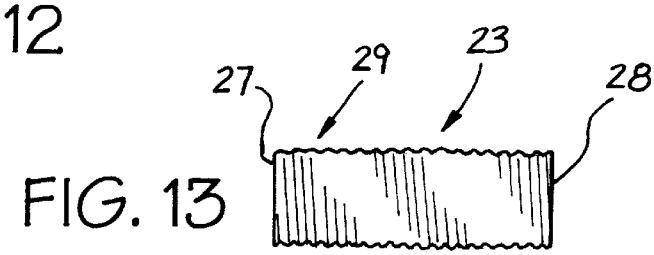

In a preferred method, the filaments 18 forming the mesh 21 are made from a thermoplastic material. If heat is applied to the tube 23 in the high-profile state, as illustrated in FIG. 12, this thermoplastic material will be heat-set to the high-profile state. Although the tube 23 can be easily expanded to a low-profile state, the heat-set characteristic will automatically bias the tube to the shorter, high-profile state with the thicker wall 31 and the increased hoop strength. As a final step in the manufacturing process, the mandrel 41 can be removed from the tube, as illustrated in FIG. 13.

When the stent 10 is heat-set providing it with characteristics which bias it to the high-profile state, there is less need to provide an external force to axially compress the stent. Thus, the insertion step illustrated in FIG. 4 can be modified by merely permitting the stent 10 to rely on its inherent characteristics to achieve the high-profile state with the thicker wall 31 and the resulting increased hoop strength.

In some cases, it may be desirable to form the corrugated tube 23 with different wall thicknesses along its length. Since the wall thickness is equated to hoop strength, this would also enable the greater hoop strength to be located where it is most needed. If the variable thickness of the wall 31 is desired, the mandrel 41 can be provided with a variable diameter, as illustrated in FIG. 14. Where the mandrel 41 has a reduced diameter, the corrugations 29 will tend to form with a greater thickness or depth. Where the mandrel 41 has the larger diameter, the corrugations 29 will have a reduced thickness, as illustrated by the reference arrow 47. Where the mandrel 41 has the smaller diameter, the corrugations 29 will have an increased thickness, as shown by the reference arrow 50. The resulting stent 10 is illustrated in FIG. 15. As a final step in this process, removal of the mandrel 41 may require some axial stretching of the stent 10 in order for the larger mandrel diameter to pass the area of increased wall thickness shown by the reference arrow 47.

Although the foregoing invention has been described with reference to preferred embodiments and preferred steps in both manufacturing and insertion methods, it will be appreciated that the stent and associated methods can be otherwise embodied. Accordingly, one is cautioned not to limit the concept to these preferred embodiments, but rather to determine the scope of the invention with reference to the following claims.

What is claimed is:

1. A vascular stent adapted to be disposed in a blood vessel of patient, comprising:

a mesh having a multiplicity of interstices and being formed in the configuration of a tube having a wall, an axis, and characteristics for moving between a low-profile state and a high-profile state;

the interstices of the mesh being generally open in the low-profile state and being generally closed in the high-profile state;

the tube in the low-profile state having an elongate configuration, with the wall having a first thickness and a first hoop strength; and the tube in the high-profile state having a compressed configuration, with the wall having a second thickness greater than the first thickness and a second hoop strength greater than the first hoop strength.

2. The vascular stent recited in claim 1 wherein:

the wall is formed with a plurality of convolutions disposed along the axis;

the convolutions in the low-profile state being generally spaced by a first distance; and the convolutions in the high-profile state being generally spaced by a second distance less than the first distance.

3. The vascular stent recited in claim 2 wherein the mesh forming the tube is a woven mesh.

4. The vascular stent recited in claim 3 wherein the woven mesh has thickness, and the wall in the low-profile state is stretched along the axis and has a thickness generally equivalent to the thickness of the woven mesh.

5. The vascular stent recited in claim 1 wherein the mesh is heatset to bias the tube to the high-profile state.

6. The vascular stent recited in claim 5 wherein the mesh is formed of a thermal plastic.

7. A stent adapted to be placed in a body conduit, comprising:

a plurality of filaments forming a mesh with interstices and a first thickness, the mesh being formed in the configuration of a tube having an axis;

the tube having a wall and being axially corrugated to facilitate a movement between a low-profile state wherein the wall has a second thickness, and a high-profile state wherein the wall has a third thickness greater than the second thickness;

the interstices being generally open when the tube is in the low-profile state, and being generally closed when the tube is in the high-profile state.

8. The stent recited in claim 10 wherein the mesh is woven.

9. The stent recited in claim 11 wherein the filaments are formed of a thermoplastic.

10. The stent recited in claim 12 wherein the thermoplastic filaments are heat-set in the high-profile state.

\* \* \* \* \*

UNITED STATES PATENT AND TRADEMARK OFFICE
CERTIFICATE OF CORRECTION

| | | |
|---|---|---|
| PATENT NO. | : 6,183,503 B1 | |
| APPLICATION NO. | : 09/399211 | |
| DATED | : February 6, 2001 | |
| INVENTOR(S) | : Charles C. Hart, John Brustad and Said Hilal | |

It is certified that error appears in the above-identified patent and that said Letters Patent is hereby corrected as shown below:

In claim 10, column 6, line 62, please change the word "heat-set" to "heatset"

Signed and Sealed this
Thirty-first Day of January, 2012

David J. Kappos
*Director of the United States Patent and Trademark Office*